United States Patent [19]

Carr, Jr. et al.

[11] Patent Number: 4,986,964

[45] Date of Patent: Jan. 22, 1991

[54] CLOT RETRACTOMETER

[75] Inventors: Marcus E. Carr, Jr.; Sheryl L. Zekert, both of Richmond, Va.

[73] Assignees: Center for Innovative Technology, Herndon; Virginia Commonwealth University, Richmond, both of Va.

[21] Appl. No.: 511,040

[22] Filed: Apr. 19, 1990

[51] Int. Cl.[5] ............................................. G01N 33/48
[52] U.S. Cl. ..................................... 422/73; 422/109; 436/69; 73/54; 73/58; 73/64.1
[58] Field of Search .................... 422/73, 109; 436/69; 73/54, 58, 64.1

[56] References Cited

U.S. PATENT DOCUMENTS

| | | |
|---|---|---|
| 3,053,078 | 9/1962 | Jewett . |
| 3,814,585 | 6/1974 | Bailly ................................. 422/73 X |
| 3,900,290 | 8/1975 | Hornstra ........................... 422/73 X |
| 3,905,769 | 9/1975 | Carroll et al. .................... 422/73 X |
| 3,918,908 | 11/1975 | Moyer et al. . |
| 4,105,411 | 8/1978 | Biver ................................... 422/73 |
| 4,317,363 | 3/1982 | Shen .................................... 73/64.1 |
| 4,319,194 | 3/1982 | Cardinal et al. . |
| 4,695,956 | 9/1987 | LeVeen et al. . |
| 4,849,340 | 7/1989 | Oberhardt . |
| 4,862,384 | 8/1989 | Bujard . |
| 4,879,432 | 11/1989 | Vieillard . |

OTHER PUBLICATIONS

"Blood"; Carr et al; 74, No. 7 399a (Abstracts 1524 and 1525).
"Platelet Contractile Regulation in an Isometric System"; Cohen et al; Nature vol. 246; pp. 36-37; 1973.
"The Structural Properties and Contractile Force of a Clot"; C. J. Jen and L. V. McIntire; Cell Motility 2; pp. 445-455; 1982.
"Peptides and Monoclonal Antibodies Which Bind to Platelet Glycoproteins IIb and/or IIIA Inhibit Clot Retraction"; T. K. Gartner and M. L. Ogilvie; Thrombosis Research 49; 49; pp. 43-53; 1988.
"Platelets and Fibrin Strands During Clot Retraction"; E. Morgenstern, U. Korell & J. Richter; Thrombosis Research 33; pp. 617-623; 1984.
"Ultrastructure of Clots During Isometric Contraction"; I. Cohen, J. M. Gerrard & J. G. White; The Journal of Cell Biology; vol. 93; pp. 775-787; 1982.
"Separable Function of Platelet Release Reaction and Clot Retraction"; Y. Yatomi et al; Biochemical and Biophysical Research Communications 140; pp. 329-334; 1986.
"The Effect of Dextran 70 on the Structure of Plasma-Derived Fibrin Gels"; M. Carr & D. A. Gabriel; Univ. of N.C.; pp. 985-993; 1980.
"Biorheology in the Practice of Medicine: Resonance Thrombography"; H. Hartert; Biorheology 21; pp. 19-32; 1984.

*Primary Examiner*—Robert J. Warden
*Assistant Examiner*—Stephanie Blythe
*Attorney, Agent, or Firm*—Whitham & Marhoefer

[57] ABSTRACT

An instrument for measuring the internal force characteristics of a blood sample (12) during clotting has been developed. The blood sample (12) is held between a cup (10) and a plate (16). The plate (16) is connected to a force displacement transducer (22). As the clot forms, platelets contract and exert an inward pulling force on the plate (16). This inward pulling force is sensed by the transducer (22) which outputs a corresponding voltage signal. The voltage signal is amplified (24) and recorded on strip chart paper (28). The voltage signal (32) can be directly translated into force parameters by first calibrating the instrument with standard weights. It has been found that the maximum force measurements are obtained under controlled temperature, ionic strength and calcium concentration conditions which approximate those of the blood while in the body. A particular feature of the invention includes a water jacket (14) which is used to maintain the temperature of the blood sample (12) at 37° C. (body temperature).

15 Claims, 3 Drawing Sheets

CLOT RETRACTOMETER

BACKGROUND OF THE INVENTION

1. Field of the Invention

The present invention is generally related to instrumentation and techniques used for continuously measuring isometric force development during blood clot retraction.

2. Description of the Prior Art

In vivo clotting is known to involve both platelet-mediated, primary, and plasma protein (fibrin)-mediated, secondary, hemostasis. While this artificial separation has allowed simplification of various experimental systems, it is well recognized that neither process occurs as an isolated event. When vascular injury occurs, basement membrane is exposed and platelets adhere thereto. Platelet attachment is followed by attachment of fibrinogen to platelet membrane receptors. When attached to the platelet membrane receptors, fibrinogen serves as a molecular bridge between platelets which promotes further aggregation of platelets at the point of injury. As aggregation proceeds, clot promoting substances are released from the platelet mass which promote formation of fibrin strands. Fibrin reinforces the platelet plug to halt blood loss.

Once the fibrin network is in place, the platelets begin to actively pull on the network strands. The pulling force is directly related to the contraction of microfilaments in the platelet cells. Contraction of the microfilaments is dependent on the intracellular cyclic adenosine monophosphate (cAMP) concentration. The platelets are connected to the fibrin strands by psuedopods; therefore, as the platelets constrict, the fibrin strands are pulled inward. When viewed in vitro, this process, called clot retraction, leads to a dramatic reduction in clot volume. Clot retraction is an irreversible process. It is assumed that clot retraction plays a role in approximating the edges of a tissue defect and in concentrating the clot precisely in the injured area. The platelet-fibrin network subsequently serves as the scaffolding for tissue repair.

Material released from platelets is known to affect fibrin assembly and structure. Platelet Factor 4 (PF4), a protein released from platelet alpha-granules, speeds fibrin clotting and results in thick fiber formation. Thrombospondin, a protein also from the alpha-granules, speeds fibrin formation but causes thinner fiber formation. The addition of platelet extract, prepared by sonicating platelets, to clotting fibrin results in thinner fibers which are more resistant to fibrinolysis. When intact platelets are added to clotting fibrin, thicker fibers are produced and clot dissolution by plasmin is enhanced. The presence of intact platelets also leads to clot retraction and an increased storage elastic modulus.

It is known that intact glycoprotein IIb/IIIa (GPIIb/IIIa) complexes must be present on the platelet surfaces for clot retraction to proceed. Congenital absence of GPIIb/IIIa or blockade of GPIIb/IIIa by synthetic peptide analogues of fibrinogen or by monoclonal antibodies is known to result in absent or reduced clot retraction. In addition, an intact A chain of fibrinogen and adequate calcium are required for clot retraction.

Clot retraction may be inhibited by several mechanisms. High thrombin and/or fibrin concentrations both reduce the extent of clot retraction. Manganesium chloride ($MgCl_2$) inhibits clot retraction and may operate by competing with calcium. Substances which increase intracellular cAMP such as dibutyryl cAMP (DBcAMP) and prostaglandin $E_1$ inhibit clot retraction. As noted above, constriction of the microfilaments is dependent on the cAMP concentration. Cytochalsin E and B, which alter filamentous actin, inhibit clot retraction, while colchicine and vinblastine, which disrupt microtubules, have only a minimal effect. Aspirin and indomethacin, which are commonly used antiplatelet agents, do not inhibit clot retraction.

Several techniques have been used to measure clot retraction. The first and most common method is to measure the volume of excluded material and then calculate the percentage of the residual clot volume. This technique, while simple, does not allow measurement of the forces involved in clot retraction nor does it allow detection of the onset of force generation. Other researchers have recorded force measurements by forming cylinders or strips of clot which are subsequently anchored at one end and attached at the other end to a transducer or a mechanical recording device. This technique is reminiscent of studies on smooth muscle contraction and allows suspension of the clot in a bathing solution. Changing the solution provides a way of exposing the clot to a variety of retraction altering agents. Unfortunately, the two end-anchored clot technique does not allow detection of the onset of force development and suffers from the need to manipulate the clot. Clot manipulation can result in "passive" fibrin retraction which is independent of platelet activity. A third technique utilizes a fluids rheometer to measure normal force development during plasma gel clotting and retraction. While the rheological method does allow measurement of both the onset and the kinetics of force development, rheometers are extremely expensive devices which require quite a bit of training to use properly.

Atherosclerosis and malignancy are primary causes of morbidity and mortality in the aging American population. Many complications, perhaps even the pathogenesis of atherosclerosis, are intimately related to clotting. Cerebral vascular accidents and myocardial infarctions are direct results of inappropriate clot deposition. Malignancy is known to be a "hypercoagulable" state associated with increased frequency of deep venous thrombosis and pulmonary embolus. Primary modes of therapy in patients suffering the above conditions involve the prophylactic use of antiplatelet agents or anticoagulants, or the emergent use of thrombolytics. A need exists for a simple, low cost instrument which can help define the interactions between platelets and fibrin and to assess how these interactions impact on the eventual clot removal. This information is necessary for rational use of available therapy and is essential to the development of newer modes of treatment.

SUMMARY OF THE INVENTION

It is therefore an object of the present invention to provide a simple, low cost, easy to use instrument which can quantitatively measure force development during clot retraction.

It is another object of this invention to provide an instrument which can be used to evaluate a variety of clot properties.

It is still another object of this invention to establish the conditions under which repeatable results can be obtained when using the novel clot retractometer instrument.

According to the invention, instrumentation has been developed which measures force development during clot retraction. Clots are formed between a stainless steel plate and cup. As the clot forms, it attaches to the inner walls of the cup and the bottom and side walls of the plate. The plate is connected to a force displacement, strain gauge transducer. As the fibrin strands are pulled taut under the influence of microtubule platelet contraction, a retraction force is placed directly on the plate to which the clot adheres. The retraction force exerted on the plate results in a voltage change being produced by the connected strain gauge. The voltage signal from the strain gauge is then converted to a quantity of force, i.e., dynes/cm$^2$. The ability to convert the voltage signal into a force quantity is achieved by calibrating the strain gauge using standard weights.

A variety of clot properties can be evaluated with this instrument. In particular, the lag phase (LP) prior to force development, the maximum rate of force development (MRFD), and the maximum force generated (MFG) can all be determined during clot retraction using this instrument. In addition, a variety of test conditions have been shown to affect measurements with this instrument. In particular, the platelet count, ionic strength, pH, calcium concentration, thrombin concentration, temperature, and gap distance between the plate and cup can all affect the measured clot property. Therefore, an ideal set of conditions for determining clot properties has been established.

BRIEF DESCRIPTION OF THE DRAWINGS

The foregoing and other objects, aspects and advantages will be better understood from the following detailed description of the preferred embodiment of the invention with reference to the drawings, in which.

DETAILED DESCRIPTION OF A PREFERRED EMBODIMENT OF THE INVENTION

Figure 1:
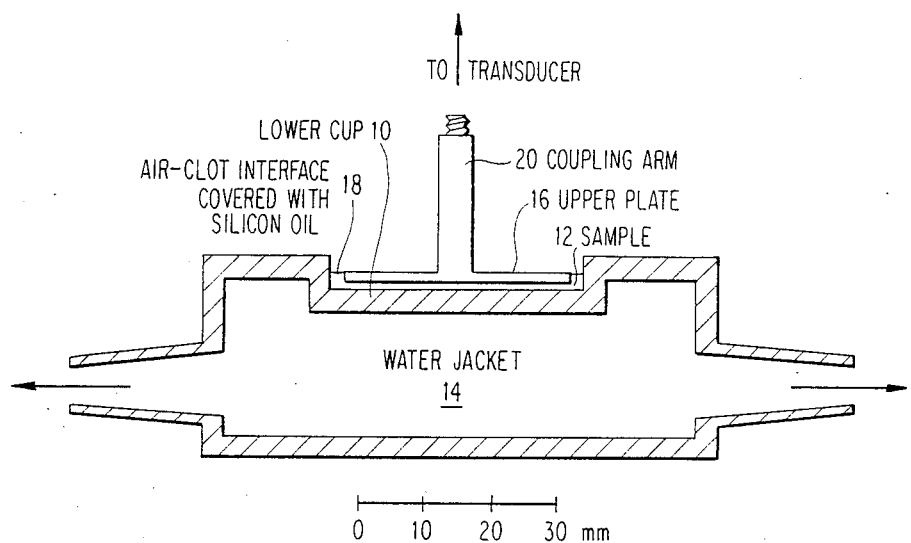
FIG. 1 is a partial side view of an instrument used to measure force development during platelet mediated clot retraction.

Referring now to the drawings, and more particularly to FIG. 1, there is shown a lower cup 10 in which a blood sample 12 is placed for testing its clot retraction properties. The cup 10 is thermostatically controlled by a heat transfer media passing through water jacket 14. Prior to gelation, upper plate 16 is centered above the cup and lowered into the blood sample 12. The air-clot interface 18 between the upper plate 16 and the lower cup 10 is covered with silicon oil to prevent evaporation during measurement. Suitable silicon oil is available from the Dow Corning company of Midland, Michigan (sold as Medical Fluid 360, 20 centistokes). The upper plate 16 is connected to a force displacement transducer (not shown) by coupling arm 20.

When a blood sample 12 is clotted within the lower cup 10, fibrin forms, platelets adhere to fibrin strands and the clot adheres to the stainless steel instrument surfaces. Platelets extend pseudopodia along the fibrin strands and subsequently pull the fibrin strands inward towards themselves. Force development occurs via microtubule contraction utilizing the energy of cell metabolism. As the fibrin strands are pulled taut, forces are transmitted throughout the network to the lower cup 10 and upper plate 16 surfaces.

Figure 2:
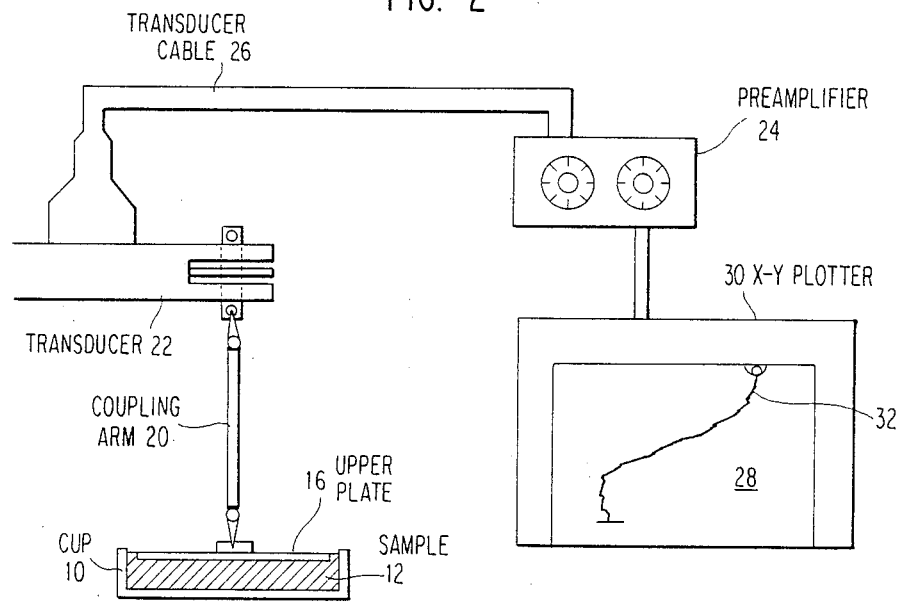
FIG. 2 is a schematic drawing of the instrument used to measure force development during platelet mediated clot retraction.

FIG. 2 shows that forces acting on upper plate 16 are transmitted to a force displacement transducer 22 via the coupling arm 20. In a preferred embodiment, the force displacement transducer is a GRASS, Model FT 03 strain gauge available from Grass Instrument, Company of Quincy, Mass. As trapped platelets pull on the upper plate 16, a small displacement of the transducer 22 arm results in voltage generation proportional to the force applied. A preamplifier 24 powers the transducer 22 and the voltage signal from the transducer 22 is sent to the preamplifier 24 for by transducer cable 26 for amplification The preamplifier 24 may be a Model AT available from the Gould company of Cleveland, Ohio. The amplified signals output from the preamplifier 24 are recorded on strip paper 28 on an X-Y plotter 30.

The graph 32 of the voltage signal presented on strip paper 28 corresponds directly with the force the blood clot 12 exerts on the upper plate 16. The voltage signal produced by the transducer 22 is translatable directly into units of force, i e., dynes/cm$^2$, by calibrating the instrument. Calibration is achieved by suspending standard weights from the transducer arm 22 and recording the signal output. Since a known force can be calculated from the known mass of the standard weight and the gravitational force, the voltage signals output on the strip chart 28 are determined to correspond to the known force. Hence, the signals output from the transducer 22 during a clotting experiment on blood sample 12 are simply compared to the signals achieved with the standard weights.

Of key importance to this invention is the fact that the blood sample 12 is positioned in a small, relatively constant, volume created by the lower cup 10 and upper plate 16. If the blood sample 12 were stored in a volume with movable and porous surfaces, clot shrinkage would occur and serum would be expressed. If the blood sample 12 were stored in a volume with immovable surfaces, sufficient force may develop to detach the clot. Detachment of the clot would be followed by clot shrinkage and serum expression. In the present invention, the surfaces are immovable (i.e, the cup 10 and the plate 16) and the gap width between the cup 10 and the upper plate 16 is small (i.e., 1 millimeter, 1 mm). This arrangement avoids early gel detachment during initial force development. Clot detachment may occur late in a measurement, but it is easily identified as a sudden drop in force.

Experiments have been performed which show that the conditions under which a blood sample 12 is tested affect the measured force properties of the clot. In particular, when controlled for platelet count, ionic strength, pH, calcium concentration, thrombin concentration, temperature and gap distance, measurements for the lag phase prior to force development, maximum rate of force development and maximum force generated are reproducible.

During the experiments, blood was obtained via sterile venipuncture and was anticoagulated with sodium citrate (3.8%). Platelet rich plasma (PRP) was prepared by centrifugation at 500 g for five minutes at room temperature. The platelet count of the PRP was determined using a Coulter Counter Model ZM available from the Coulter company of Hialeah, Fla. Platelet poor plasma (PPP) was prepared by centrifugation at 1500 g for fifteen minutes. The standard clotting conditions included: ionic strength of 0.15 molar (M), pH of 7.4 (achieved using 0.05 M Tris buffer available from Sigma Diagnostics of St. Louis, Mo.), calcium concentration of 10 mM, thrombin concentration of 1.5 NIH u/ml, and a temperature of 37° C. with a final volume of 2.00 milliliters (ml). The desired platelet concentration was established by diluting PRP with PPP. Plasma samples were placed in the lower cup and brought to a final volume of 1.9 mls by the addition of prewarmed Tris buffered saline. The solution was allowed to equilibrate at the cup 16 temperature for one 15 minute (i.e, a 37° C. heat transfer media passes through the water jacket 14). Clotting was initiated by the addition of thrombin and calcium resulting in a final volume of 2.0 mls. Immediately after the addition of thrombin, the upper plate 16 was placed in the clotting solution. As the lower cup 10 is raised into position, a stop (not shown) attached to the upper surface of the lower cup 10 comes to rest against the transducer 22 housing setting the gap between the lower cup 10 25 and the upper plate 16 at 1 mm.

Figure 3:
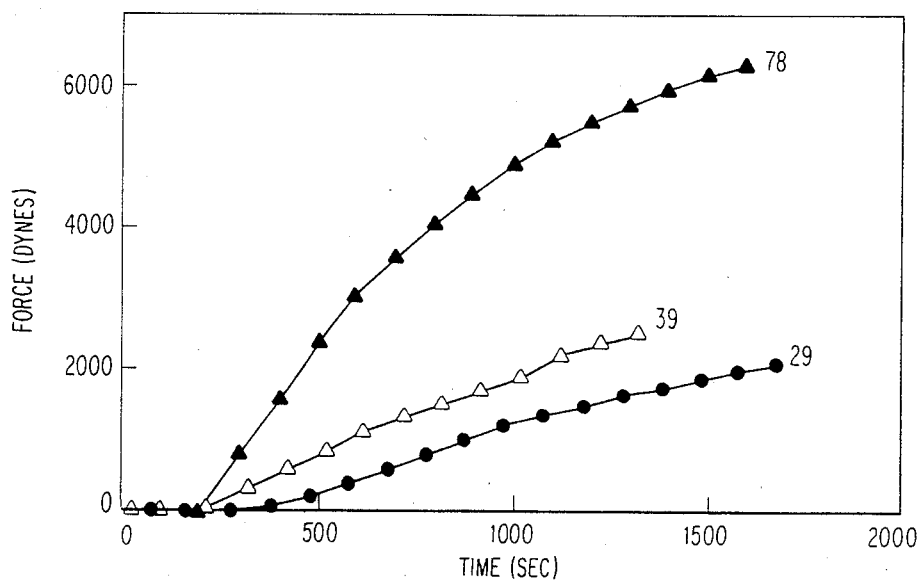
FIG. 3 is a graph showing the effect of platelet concentration on clot retraction.

FIG. 3 shows the effect of differing platelet concentrations on measured force parameters. Clots were formed directly in the refractometer by the addition of thrombin and calcium to three different buffer solutions of PRP. In particular, the three buffer solutions contained concentrations of 29,000, 39,000, and 78,000 platelets per microliter. Each solution produced obvious force development after a lag phase of about 200 seconds. FIG. 3 shows the rate of force development and the total force developed were platelet concentration dependent. For example, the initial rate of force development increased from 1.8 to 2.5 to 8.0 dynes/sec as the platelet concentration increased from 29,000 to 39,000 to 78,000 platelets per microliter, respectively. Likewise, he force developed at one thousand seconds increased from 1250 to 1850 to 4800 dynes over the same platelet concentration range.

From FIG. 3 it can be said that samples with larger platelet concentrations are preferred, since they have a correspondingly larger force affect in the clot retractometer. In addition, to compare the force characteristics of different samples, each sample must have a similar concentration of platelets. For example, a standard force response for normal blood could be established at 45,000 platelets per microliter. Then, a sample of blood from a patient suffering a blood disorder, i.e., anemia, would be prepared by first preparing PRP and PPP samples and then diluting the PRP sample to achieve a test sample having 45,000 platelets per microliter. At this point, force difference between the standard and the test sample would have some meaningful significance.

Figure 4:
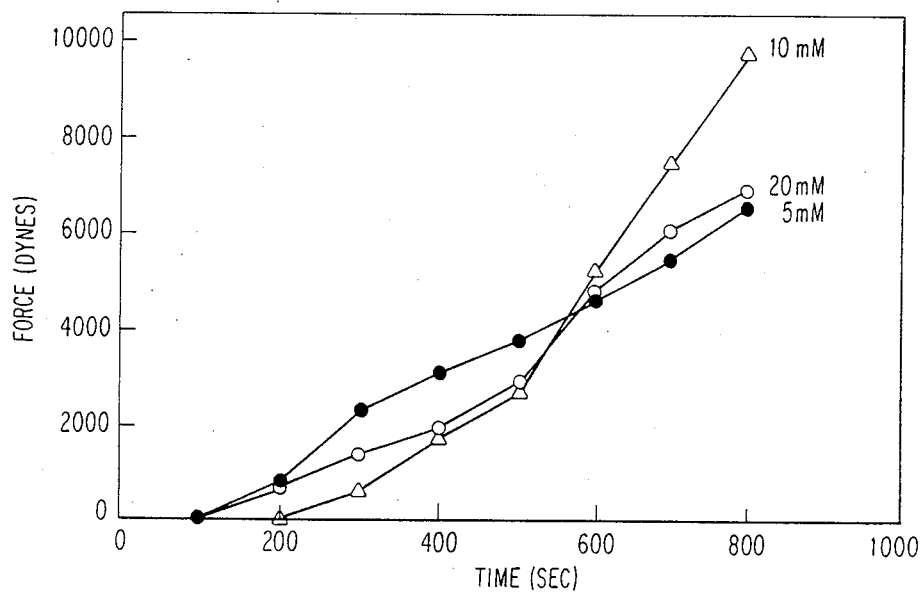
FIG. 4 is a graph showing the effect of calcium on clot retraction.

FIG. 4 shows that varying the calcium concentration in the blood sample produces slight changes in the measured force characteristics The calcium concentration of three blood samples, each of which contained 78,000 platelets per microliter, was adjusted by adding an appropriate amount of a dilute solution of calcium chloride ($CaCl_2$), i.e. 0.50 M $CaCl_2$, to each sample. In particular, the samples had concentrations of 5 mM, 10 mM and 20 mM calcium, respectively. FIG. 4 shows that for concentrations between 5 and 20 mM, calcium has minimal affect on the lag phase, the initial rate of force development, or the total force developed. Optimum force development consistently occurred in samples containing 10 mM $CaCl_2$. Parallel aggregation studies were done with pH, ionic strength, and fibrinogen concentration. Such studies were not performed with calcium because the addition of calcium causes clotting, and thus prevents aggregation measurements. Turbidity measurements demonstrated increasing fibrin fiber mass/length ratio over the same calcium range.

Figure 5:
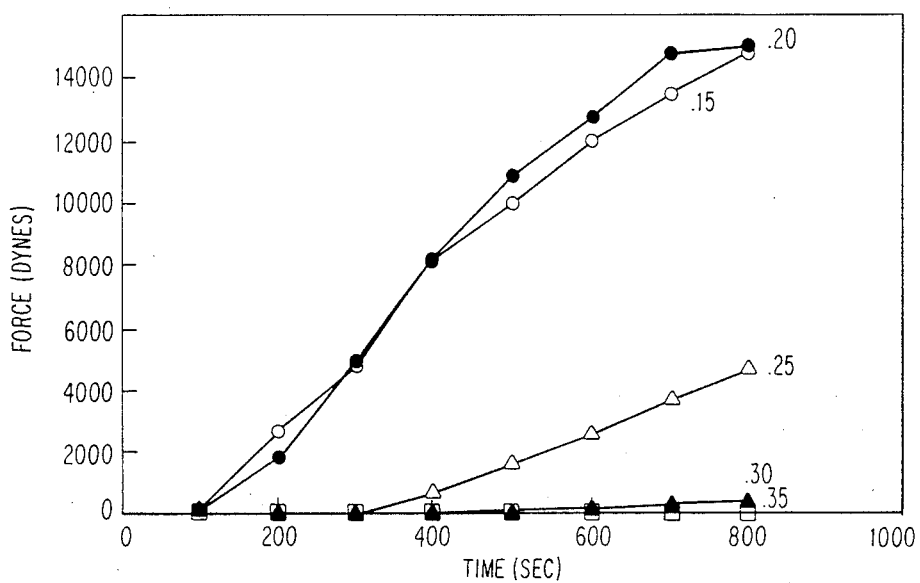
FIG. 5 is a graph showing the affect of ionic strength on clot retraction.

FIG. 5 shows that altering inic strength in a blood sample dramatically alters the measured force characteristics for platelet-mediated clot retraction. The ionic strength of four blood samples, each of which contained 78,000 platelets per microliter, was adjusted by adding appropriate amounts of 1 M NaCl to each sample. In particular, the four blood samples had ionic strengths of 0.15 M, 0.20 M, 0.25 M, and 0.35 M, respectively. FIG. 5 shows that increasing the ionic strength from 0.15 M to 0.20 M has minimal affect on the lag phase, the initial rate of force development, or the total force developed; however, above an ionic strength of 0.20 M the lag phase is increased, and both the initial rate of force development and the total force developed are decreased. The lag phase increased from 100 to 300 to 400 seconds as the ionic strength increased from 0.20 M to 0.25 M to 0.30 M, respectively. Over the same ionic strength range, the initial rate of force development declined from 27.4 to 9.3 to 0.87 dynes/sec and the total force developed at 800 seconds fell from 15,070 to 4,640 to 350 dynes, respectively. At an ionic strength equal to 0.35 M, clot formation did not occur during the measurement period. Platelet aggregation studies were unaffected by increasing the ionic strength from 0.15 M to 0.35 M. Turbidity measurements revealed reduction in fibrin fiber mass/length ratios with increasing ionic strength in gels (clots) formed from platelet rich plasma.

Although insufficiently studied to this point, fibrin structure is critical to the retraction process. The extent of clot retraction is inversely related to, and maximum tension development is dependent, on fibrin concentration. The importance of fibrin's molecular structure has been intimated by several findings: factor XIII mediated crosslinking is critical to tension development; high thrombin concentrations, known to influence fibrin structure, inhibits clot retraction; and expression of serum is mediated by gel pores, and gel pore size is directly related to fibrin fiber diameter. Thus, the extent of clot retraction is probably a function of fiber diameter.

The marked dependence of clot retraction on ionic strength demonstrated in FIG. 5 is consistent with the postulate that clot retraction is a function of fiber diameter Fibrin fiber mass/length ratio, an indicator of fiber diameter, is an inverse function of ionic strength. As the ionic strength increases, fiber diameter decreases. Gels with thin fibers are clear, have small pores, and retain water. Since platelet function, as measured by platelet aggregation, does not change as ionic strength increases from 0.15 M to 0.35 M; the changes in clot retraction illustrated in FIG. 5 are most likely mediated by altered fibrin structure.

Figure 6:
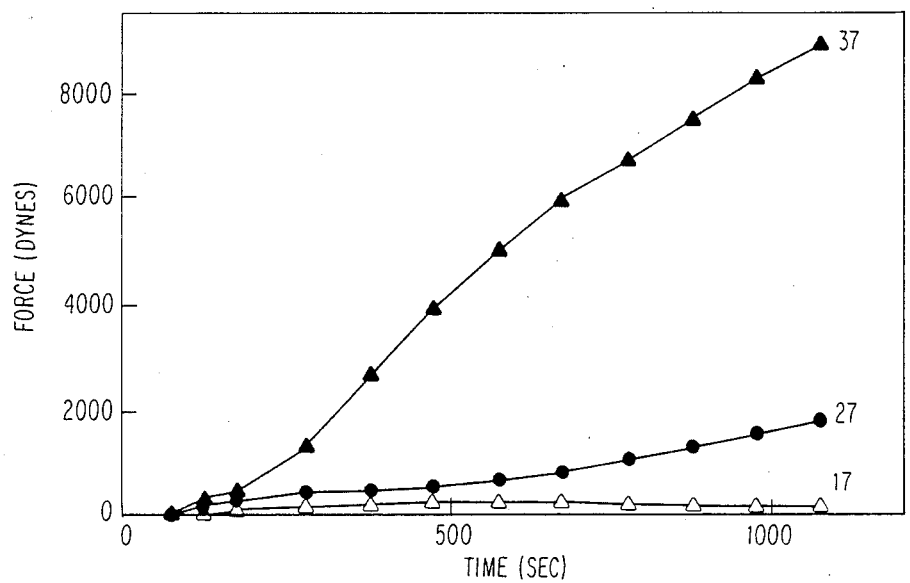
FIG. 6 is a graph showing the effect of temperature on clot retraction.

FIG. 6 shows that the temperature at which blood samples are tested with the clot retractometer greatly affects the measured force characteristics. Three blood samples, each of which contained 78,000 platelets per microliter, were tested in the clot retractometer at 37° C., 27° C. and 17° C. FIG. 6 shows that temperature has a minimal effect on the lag phase, but dramatically causes decreases in both the initial rate of force development and the total force developed. At 37° C., the initial rate of force development of force development was 11.8 dyne/sec and the total force at 1000 seconds was 8,860 dynes. Decreasing the temperature to 27° C. resulted in a decrease in the initial rate of force development to 2.6 dynes/sec and dropped the total force at 1000 seconds to 1840 dynes. At 17° C., minimal force development was detected. Previous turbidity studies have demonstrated minimal impact of temperature on fibrin clotting over the range of 17° C. to 37° C.

The dramatic temperature dependence of clot retraction shown in FIG. 6 is a new finding but it is in agreement with previous reports. For example, it has been reported that cooling platelet rich plasma to 4° C. produces a reversible inhibition of clot retraction and that heating platelet rich plasma to 42° C. produces irreversible changes in platelet morphology and irreversible inhibition of clot retraction.

The above experiments, illustrated in FIGS. 3-6, show that clot retraction is maximal under physiologic conditions. The ionic strength of plasma is approximately 0.15 M. Shifts upward are known to cause changes in the erythrocyte volume and shifts downward are known to cause erythrocyte rupture (hemolysis). Therefore, the ionic strength of a blood sample being measured should be between 0.10 and 0.20. The normal body temperature lies between 35° C. and 39° C. The experiments performed show that shifts toward room temperature (i.e., 27° C.) markedly inhibit retraction. Other investigators have shown irreversible changes in platelet function at temperatures above 40° C. Therefore, retraction measurements on blood samples should be made at approximately 37° C. The fibrinogen concentration of the sample should be considered since other investigators have shown clot retraction to be inhibited by either high or low fibrinogen concentration. The physiologic norm for blood is a pH of 7.4 and blood is buffered so well that shifts from pH 7.4 are very unusual. Therefore, to be physiologically relevant, clot retraction measurements should be done at pH 7.4.

The clot retractometer used in these experiments is simple in design, easy to use, and sensitive. The clot retractometer design avoids many of the problems inherent to previous techniques of quantitating clot retraction. The measurement made in the clot retractometer is isovolemic and thus avoids passive retraction. Measurement is possible from the moment of clot formation, thus allowing both the kinetics of force development and the total force developed to be measured. Either whole blood or platelet rich plasma are suitable for testing in the clot retractometer.

While the invention has been described in terms of its preferred embodiment which includes a thermostated cup for retaining blood samples and an upper plate connected to a GRASS force displacement transducer, those skilled in the art will recognize that the invention can be practiced with modification within the spirit and scope of the appended claims.

Having thus described our invention, what we claim as new and desire to secure by Letters Patent is as follows:

1. An instrument for measuring the retraction force characteristics of a blood clot, comprising:
   a means for holding a blood sample between a pair of parallel plates position a fixed distance apart, said means for holding said blood sample comprising a side wall attached to one of said plates which forms an open top cup with said plate, another of said plates fitting within said open top cup and having an outer periphery spaced from said side wall, each of said plates capable of being in contact with said blood sample such that platelets in said blood sample can adhere to each of said plates; and
   a means for sensing a pulling force exerted on one of said plates pulling said plates towards each other as said blood sample forms a blood clot, said means for sensing producing an electric signal proportional to said pulling force.

2. An instrument as recited in claim 1 further comprising a means for controlling the temperature of said blood sample while it is positioned between said parallel plates.

3. An instrument as recited in claim 2 wherein said means for controlling the temperature of said blood sample comprises a jacket and a means for passing a heat transfer media through said jacket said jacket surrounding said means for holding said blood sample.

4. An instrument as recited in claim 1 wherein said means for sensing comprises a force displacement transducer mechanically connected to one of said plates.

5. An instrument as recited in claim 4 further comprising a means for amplifying an electrical signal from said force displacement transducer and a means for displaying the amplified electrical signal.

6. An instrument as recited in claim 5 wherein said means for displaying comprises an X-Y plotter and strip chart paper.

7. A method for determining the retraction force characteristics of a blood sample during clotting, comprising the steps of:
   positioning a blood sample between a pair of parallel plates which are a fixed distance apart which allows platelets in said blood sample to adhere to both of said plates;
   maintaining the temperature of said blood sample between 35° C. and 39° C.; and
   monitoring a pulling force exerted on one of said plates pulling said plates towards each other while said blood sample is clotting.

8. A method as recited in claim 7 wherein said step of maintaining maintains said temperature at approximately 37° C.

9. A method as recited in claim 7 further comprising the step of adjusting the calcium concentration of said blood sample to be within the range of five millimolar and twenty millimolar.

10. A method as recited in claim 9 wherein said step of adjusting the calcium concentration adjusts the calcium concentration to be approximately ten millimolar.

11. A method as recited in claim 7 further comprising the step of adjusting the ionic strength of said blood sample to be within the range of 0.10 M and 0.20 M.

12. A method as recited in claim 11 wherein said step of adjusting the ionic strength adjusts the ionic strength to be approximately 0.15 M.

13. A method as recited in claim 7 further comprising the step of determining the lag phase prior to force development caused by said inward pulling force of said blood sample during clotting.

14. A method as recited in claim 7 further comprising the step of determining the maximum rate of force development caused by said inward pulling force of said blood sample during clotting.

15. A method as recited in claim 7 further comprising the step of determining the maximum force generated caused by said inward pulling force of said blood sample during clotting.

* * * * *